United States Patent
Ali et al.

(10) Patent No.: US 10,886,022 B2
(45) Date of Patent: Jan. 5, 2021

(54) SYSTEM AND METHOD FOR AUTHENTICATING DISPOSABLE COMPONENTS IN EXTRACORPOREAL PHOTOPHERESIS

(71) Applicant: Fenwal, Inc., Lake Zurich, IL (US)

(72) Inventors: Zahra R. Ali, Chicago, IL (US); Christopher J. Wegener, Libertyville, IL (US); Tanima Jahan Abedin, Chicago, IL (US); Lan T. Nguyen, Vernon Hills, IL (US); Brian C. Nelson, Vernon Hills, IL (US); Nicole F. Young, Antioch, IL (US); Christian R. Bernard, McHenry, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/392,802

(22) Filed: Apr. 24, 2019

(65) Prior Publication Data
US 2019/0355468 A1   Nov. 21, 2019

Related U.S. Application Data

(60) Provisional application No. 62/673,714, filed on May 18, 2018.

(51) Int. Cl.
*G06K 19/00* (2006.01)
*G16H 40/40* (2018.01)
(Continued)

(52) U.S. Cl.
CPC .......... *G16H 40/40* (2018.01); *A61M 1/3681* (2013.01); *G06K 7/10366* (2013.01);
(Continued)

(58) Field of Classification Search
CPC . G16H 40/40; A61M 1/3681; A61M 2205/18; A61M 2205/50;
(Continued)

(56) References Cited

U.S. PATENT DOCUMENTS 5,868,696 A   2/1999 Giesler et al.
6,027,657 A   2/2000 Min et al.
(Continued)

FOREIGN PATENT DOCUMENTS

EP   2774685   9/2014
EP   3040093   7/2016
(Continued)

OTHER PUBLICATIONS

European Patent Office, extended European Search Report, counterpart EP App. No. 19174900.1, 9 pages (dated Sep. 16, 2019).
(Continued)

*Primary Examiner* — Matthew Mikels
(74) *Attorney, Agent, or Firm* — Cook Alex Ltd.

(57) ABSTRACT

A medical device verification system for an extracorporeal photopheresis procedure comprises a reusable irradiation device comprising a UV light source and a scanner. A fluid circuit comprises a disposable cell suspension container having a photo-reactive label comprising an identifiable code. The identifiable code is unobscured when the label in a first state and is obscured when the label is in a second state. The irradiation step is performed by irradiating the disposable cell suspension container for a predetermined period of time at or above the threshold UV irradiation level. A second input is received from the scanner during the irradiation step, the second input comprising identification of a state of the label. A response action is provided if the
(Continued)

first input comprises identification of the second state of the label and/or if the second input comprises identification of the first state of the label.

17 Claims, 12 Drawing Sheets

(51) Int. Cl.
    *A61M 1/36*      (2006.01)
    *G06K 7/10*      (2006.01)
    *G06K 19/07*      (2006.01)

(52) U.S. Cl.
    CPC ..... *G06K 19/0723* (2013.01); *A61M 2205/18* (2013.01); *A61M 2205/273* (2013.01); *A61M 2205/50* (2013.01); *A61M 2205/6054* (2013.01); *A61M 2205/6063* (2013.01); *A61M 2205/6072* (2013.01)

(58) Field of Classification Search
    CPC .. A61M 2205/6054; A61M 2205/6063; A61M 2205/6072; A61M 2205/583; G06K 7/10366; G06K 19/0723
    USPC .......... 235/435, 439, 451, 487, 491
    See application file for complete search history.

(56) References Cited

U.S. PATENT DOCUMENTS

| | | | |
|---|---|---|---|
| 7,079,230 | B1 | 7/2006 | McInerney et al. |
| 7,443,030 | B2 | 10/2008 | Waldo et al. |
| 2008/0029606 | A1* | 2/2008 | Lewis .............. G06K 19/06028 235/491 |
| 2009/0166427 | A1 | 7/2009 | Chambers |
| 2019/0006039 | A1 | 1/2019 | Ali |

FOREIGN PATENT DOCUMENTS

| | | | |
|---|---|---|---|
| WO | WO 2012/125457 | 9/2012 | |
| WO | WO 2016/057956 | 4/2016 | |
| WO | WO2017/048673 | 3/2017 | |
| WO | WO-2017048673 A1 * | 3/2017 | ............ A61M 39/12 |
| WO | WO 2017/102723 | 6/2017 | |

OTHER PUBLICATIONS

Wang et al., Nanomaterial-based barcodes, Nanoscale, 11240-11247 (May 25, 2015).

* cited by examiner

SYSTEM AND METHOD FOR AUTHENTICATING DISPOSABLE COMPONENTS IN EXTRACORPOREAL PHOTOPHERESIS

CROSS-REFERENCE TO RELATED APPLICATIONS

This application claims the benefit of U.S. Provisional Patent App. No. 62/673,714, filed May 18, 2018, which is expressly incorporated herein by reference in its entirety.

FIELD OF THE DISCLOSURE

The present disclosure relates generally to systems and methods of authenticating medical device disposable components and, in particular, to systems and methods for authenticating disposable components with photo-reactive and RFID labeling in extracorporeal photopheresis procedures.

BACKGROUND

Light irradiation therapy may be used for the treatment of various blood diseases to, e.g., eliminate immunogenicity in cells, inactivate or kill selected cells, inactivate viruses or bacteria, and/or activate desirable immune responses. For example, the photoactivatable drug psoralen may be used to treat pathogenic blood cells, such as lymphocytes, in an extracorporeal photopherisis (ECP) procedure in which the patient receives 8-methoxypsoralen (8-MOP), blood is withdrawn from the patient, the white cells separated (typically by centrifugation), and subjected to UV light to activate the 8-MOP molecules. The photoactivated 8-MOP may alter the DNA of the pathogenic leukocytes, and the fluid with the altered leukocytes may be reinfused back into the patient to induce an immune system response.

Light irradiation therapy may be performed by and/or in connection with a medical device instrument, such as an apheresis instrument. An apheresis instrument may be used to separate blood components from whole blood by passing blood of a donor/patient through the instrument to separate one or more blood components from the whole blood. The remainder of the whole blood may be returned to the circulatory system of the donor/patient and/or collected.

The medical device instrument may utilize a centrifuge and/or membrane separator to separate blood components. A disposable component may be connected to the instrument for collection of a desired blood component. The instrument hardware may have pumps, clamps, and valves that move and direct fluid or blood through the disposable component. Part of the disposable component may include a bag into which the desired blood component is collected for light irradiation therapy.

SUMMARY

According to an exemplary embodiment, the present disclosure is directed to a medical device verification system for an extracorporeal photopheresis procedure comprising a reusable irradiation device comprising a UV light source and a scanner. A fluid circuit is configured to cooperatively associate with the reusable irradiation device, the fluid circuit comprising a disposable cell suspension container having a photo-reactive label comprising an identifiable code. The identifiable code is unobscured to the scanner when the label in a first state and is obscured to the scanner when the label is in a second state. A programmable controller for the photopheresis procedure configured to receive a first input from the scanner prior to an irradiation step, the first input comprising identification of a state of the label. Based on receiving the first input from the scanner identifying the first state of the label, the irradiation step is performed by irradiating the disposable cell suspension container for a predetermined period of time at or above the threshold UV irradiation level. A second input is received from the scanner during the irradiation step, the second input comprising identification of a state of the label. Based on receiving the second input from the scanner identifying the second state of the label, the irradiation step is continued. A response action is provided if the first input comprises identification of the second state of the label and/or if the second input comprises identification of the first state of the label.

According to an exemplary embodiment, the present disclosure is directed to a medical device verification system for an extracorporeal photopheresis procedure. A reusable irradiation device comprises a UV light source and a scanner. A fluid circuit is configured to cooperatively associate with the reusable irradiation device, the fluid circuit comprising a disposable cell suspension container having a photo-reactive label comprising an identifiable code. The identifiable code is obscured to the scanner when the label is in a first state and unobscured to the scanner when the label is in a second state. A programmable controller for the photopheresis procedure is configured to receive a first input from the scanner prior to an irradiation step, the first input comprising identification of a state of the label. Based on receiving the first input from the scanner identifying the first state of the label, the irradiation step is performed by irradiating the disposable cell suspension container for a predetermined period of time at or above the threshold UV irradiation level. A second input from the scanner is received during the irradiation step, the second input comprising identification of a state of the label. Based on receiving the second input from the scanner identifying the second state of the label, the irradiation step is continued. A response action is provided if the first input comprises identification of the first state of the label and/or if the second input comprises identification of the second state of the label.

According to an exemplary embodiment, the present disclosure is directed to a computer-implemented method for approving a medical device disposable component used in an extracorporeal photopheresis procedure. A reusable irradiation device comprising a UV light source and a scanner is provided. The reusable irradiation device is configured to irradiate a target cell suspension in an irradiation step. A photo-reactive label is provided comprising an identifiable code on a disposable component configured for irradiation within the reusable irradiation device and UV light source. The identifiable code is at a first state of visibility to the scanner when not having been exposed to a threshold UV irradiation level and a second state of visibility to the scanner after being exposed to the threshold UV irradiation level. A programmable controller is provided configured to receive a first input from the scanner prior to the irradiation step, the first input comprising identification of a state of visibility of the label, and configured to receive a second input from the scanner during the irradiation step, the second input comprising identification of a state of visibility of the label. Based on receiving the first input from the scanner identifying the first state of visibility of the label, the irradiation step is performed by irradiating the disposable cell suspension container for a predetermined period of time at or above the threshold UV irradiation level. Based on receiving the second input from the scanner identifying the second state of visibility of the label, the irradiation step is continued. A response action is provided if the first input comprises identification of the second state of visibility of the label and/or if the second input comprises identification of the first state of visibility of the label.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may prevent use of counterfeit, already-used, and/or repurposed disposable components in extracorporeal photopheresis.

Some embodiments may enable instrument and/or disposable component authentication with minimal user intervention.

Some embodiments may increase difficulty in replicating authenticity markers and thereby improve copycat protection for disposable components.

Some embodiments may allow for an ECP treatment light source to be dually used also for authentication purposes.

Some embodiments may incorporate RFID tags to prevent unauthorized use.

Some embodiments may allow for an authentication label to be dually used also for verifying that irradiation has taken place.

Figure 1:
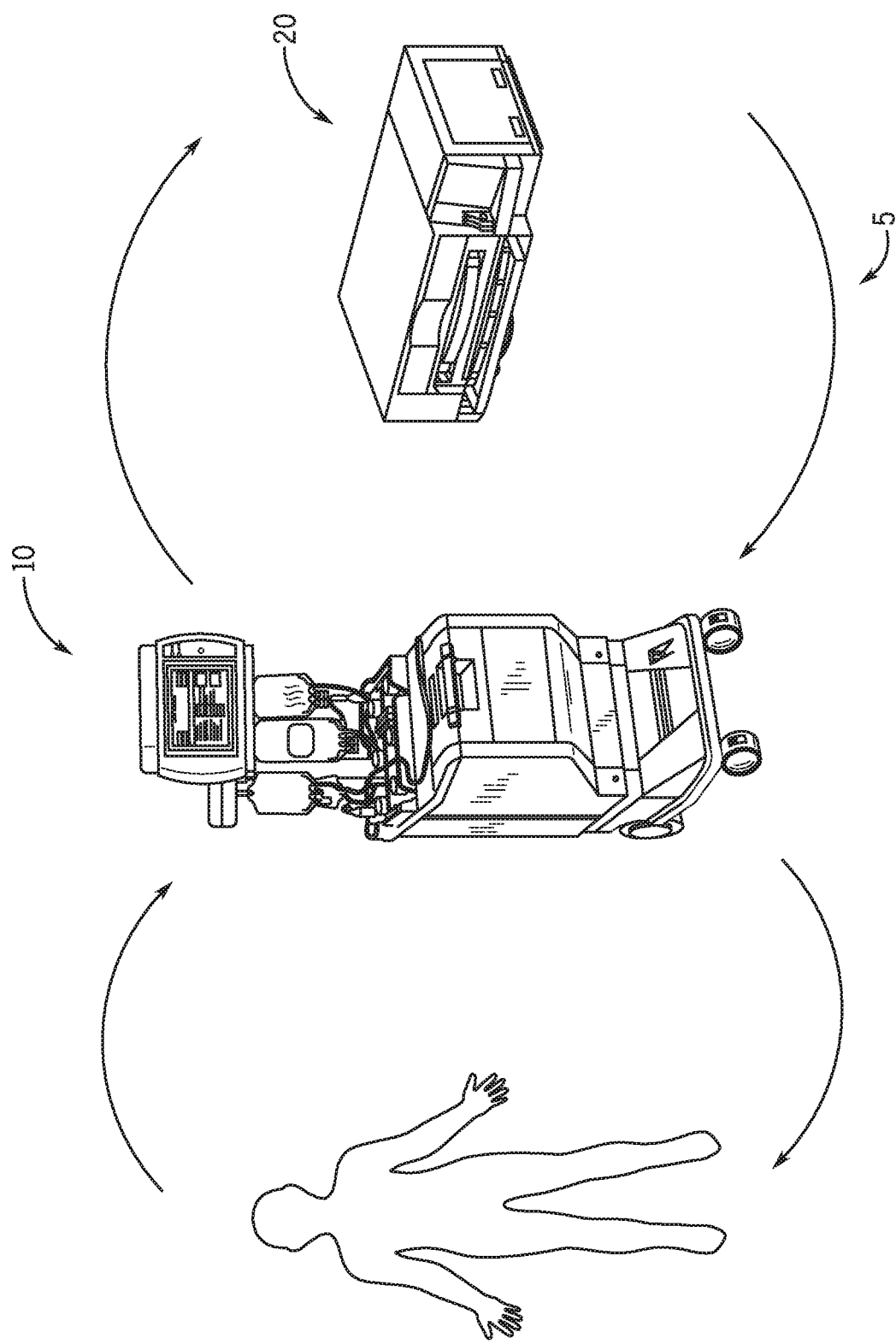
FIG. 1 is a diagram generally showing the mechanical components of a photopheresis treatment device, according to an exemplary embodiment.
Figure 2:
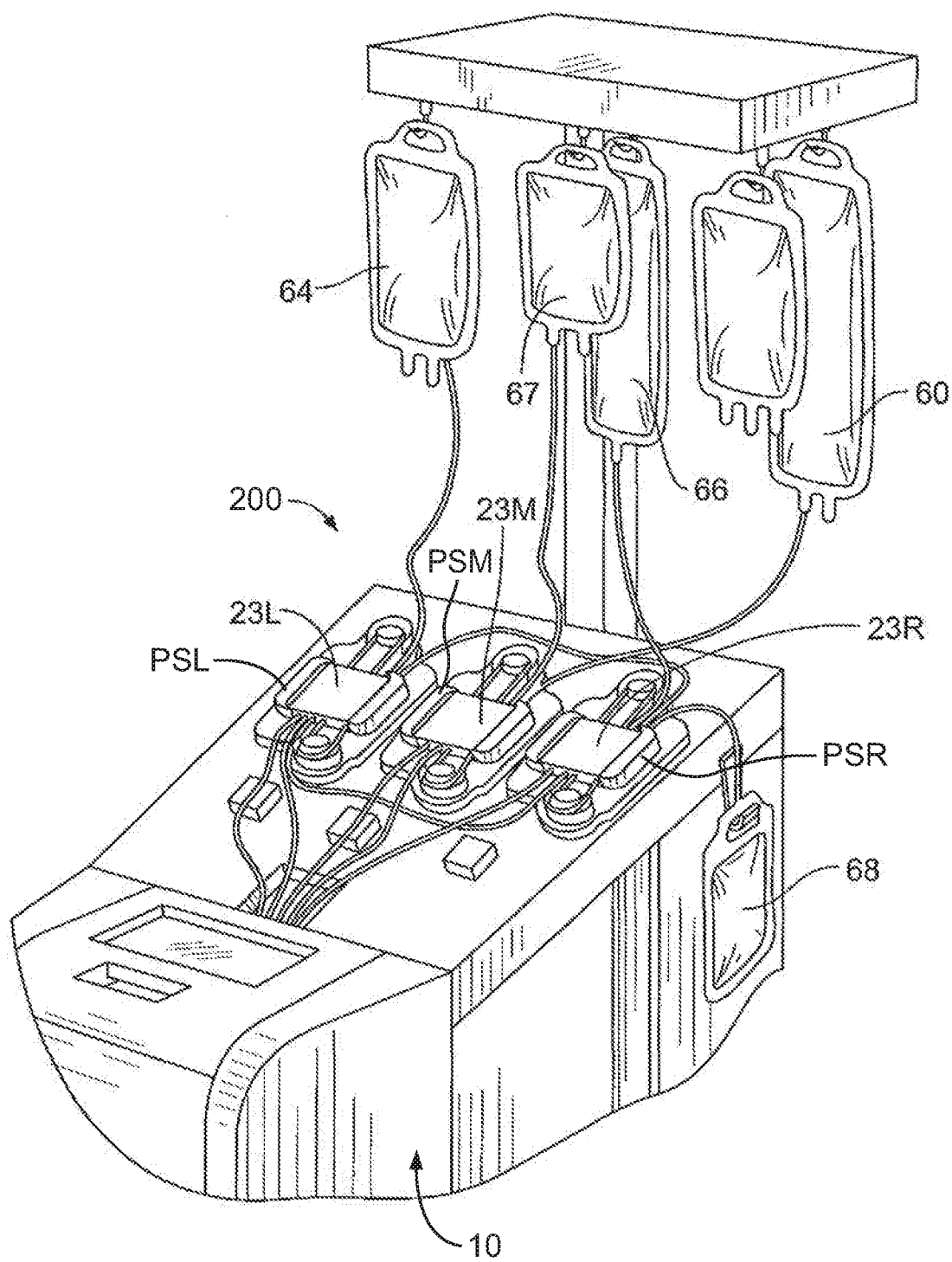
FIG. 2 is a partial perspective view of an apheresis separator useful in the methods and systems described herein, according to an exemplary embodiment.
Figure 4:
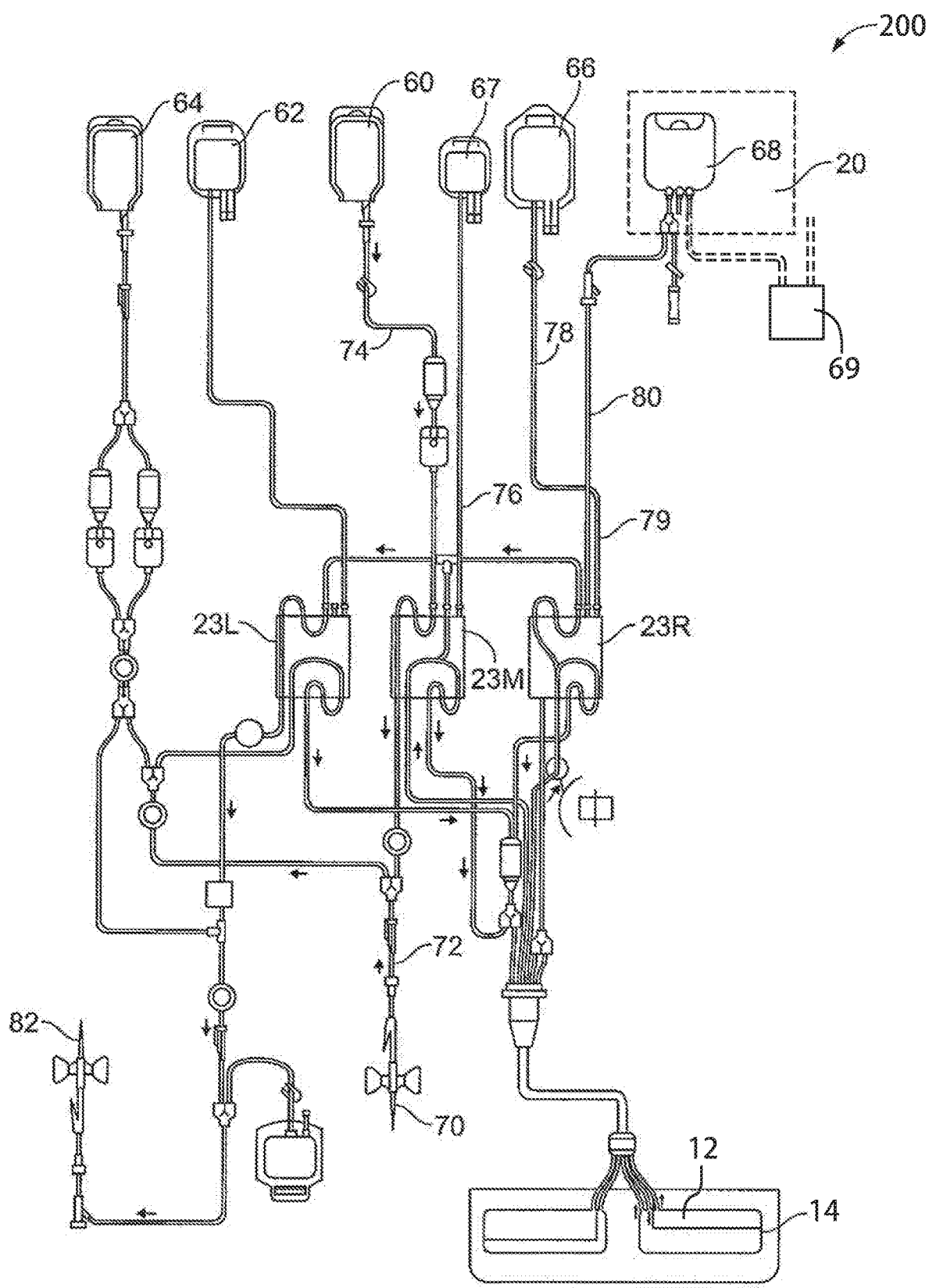
FIG. 4 is a diagram of the fluid circuit useful in the collection, treatment and reinfusion of target cells, according to an exemplary embodiment.

FIG. 1 shows, in general, the mechanical components that make up an ECP system 5 and that may be used in one or more of the methods described herein. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A blood source (e.g., donor, patient, blood container) may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as those described in greater detail in U.S. Pat. Nos. 5,868,696 and 6,027,657, and PCT Patent Application No. PCT/US2012/28492, which are hereby incorporated herein by reference in their entireties, although any suitable separation device may be used. Although the embodiments disclosed herein are described in conjunction with a separation device 10, the present embodiments may be applicable to an irradiation device 20 alone, in which case the target cell population may be provided to the irradiation device 20 subsequent to being collected elsewhere. While improved authorization/authentication systems and methods will be described herein with reference to apheresis and photopheresis, it should be understood that these principles may be employed with other medical procedures involving a specific range of light frequencies without departing from the scope of the present disclosure.

With reference to FIG. 1, whole blood may be withdrawn from the blood source and introduced into the separation component 10 where the whole blood is separated to provide a target cell population. In one embodiment, the target cell population may be mononuclear cells (MNCs) or MNCs of a particular type (lymphocytes, monocytes, and/or dendritic cells, etc.). Other components separated from the whole blood, such as red blood cells (RBCs), plasma, and/or platelets may be returned to the blood source or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cells may be collected using a device described in greater detail in the aforementioned US. Pat. No. 6,027,657. The apparatus used for the harvesting, collection and reinfusion of mononuclear cells may be a "multifunctional" automated apheresis device, as is the case with that described in U.S. Pat. No. 6,027,657. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by a hospital or medical facility.

Figure 3:
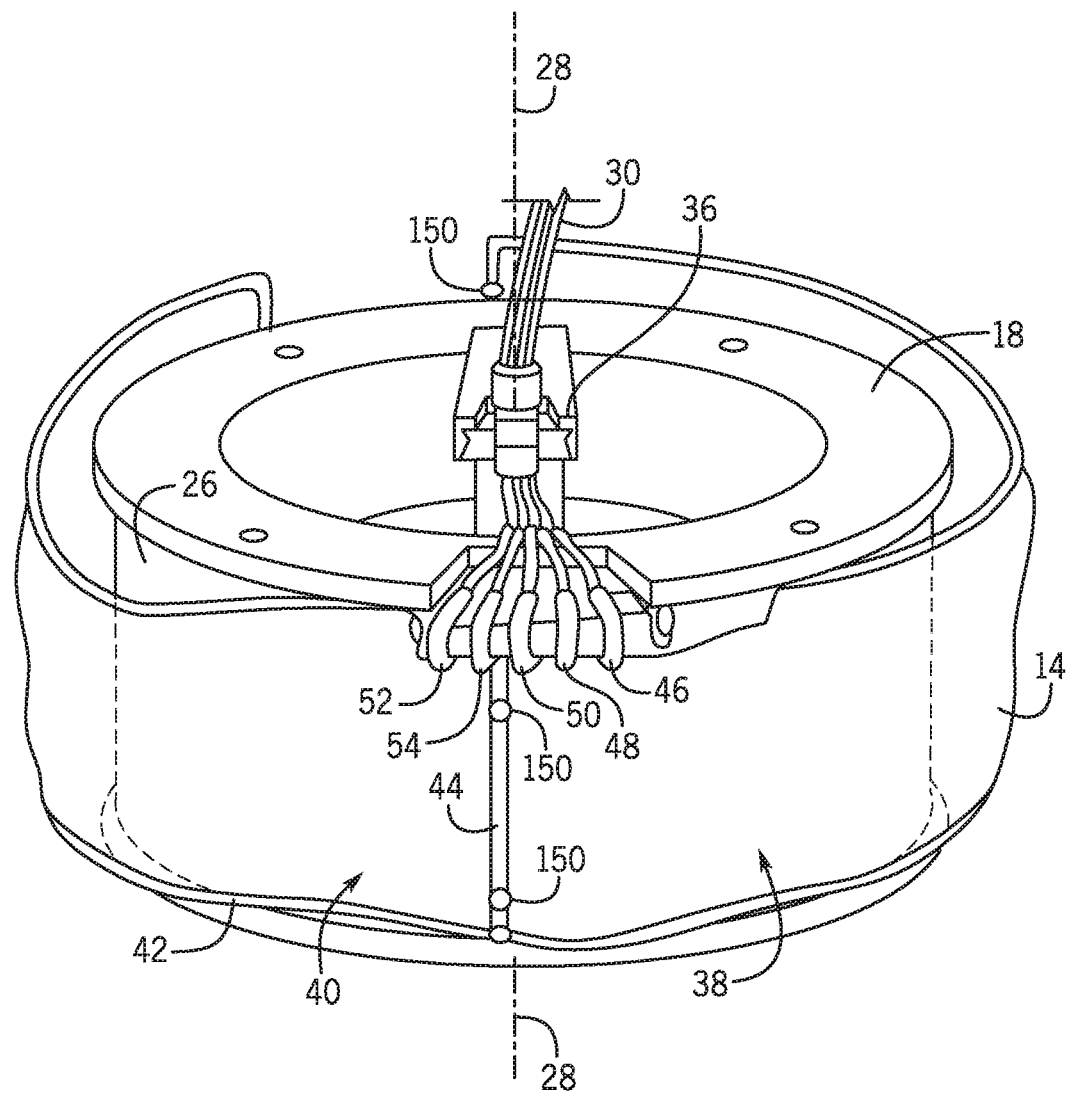
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the blood source and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more venipuncture needle(s) for accessing the blood source, e.g., the circulatory system of a patient. As shown in FIG. 4, fluid circuit 200 may include inlet needle 70 and return needle 82. In an alternative embodiment, a single needle may serve as both the inlet and outlet needle.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any irradiation device may be used. The irradiation device 20 may include a tray or other holder for receiving one or more containers during treatment.

Figure 5:
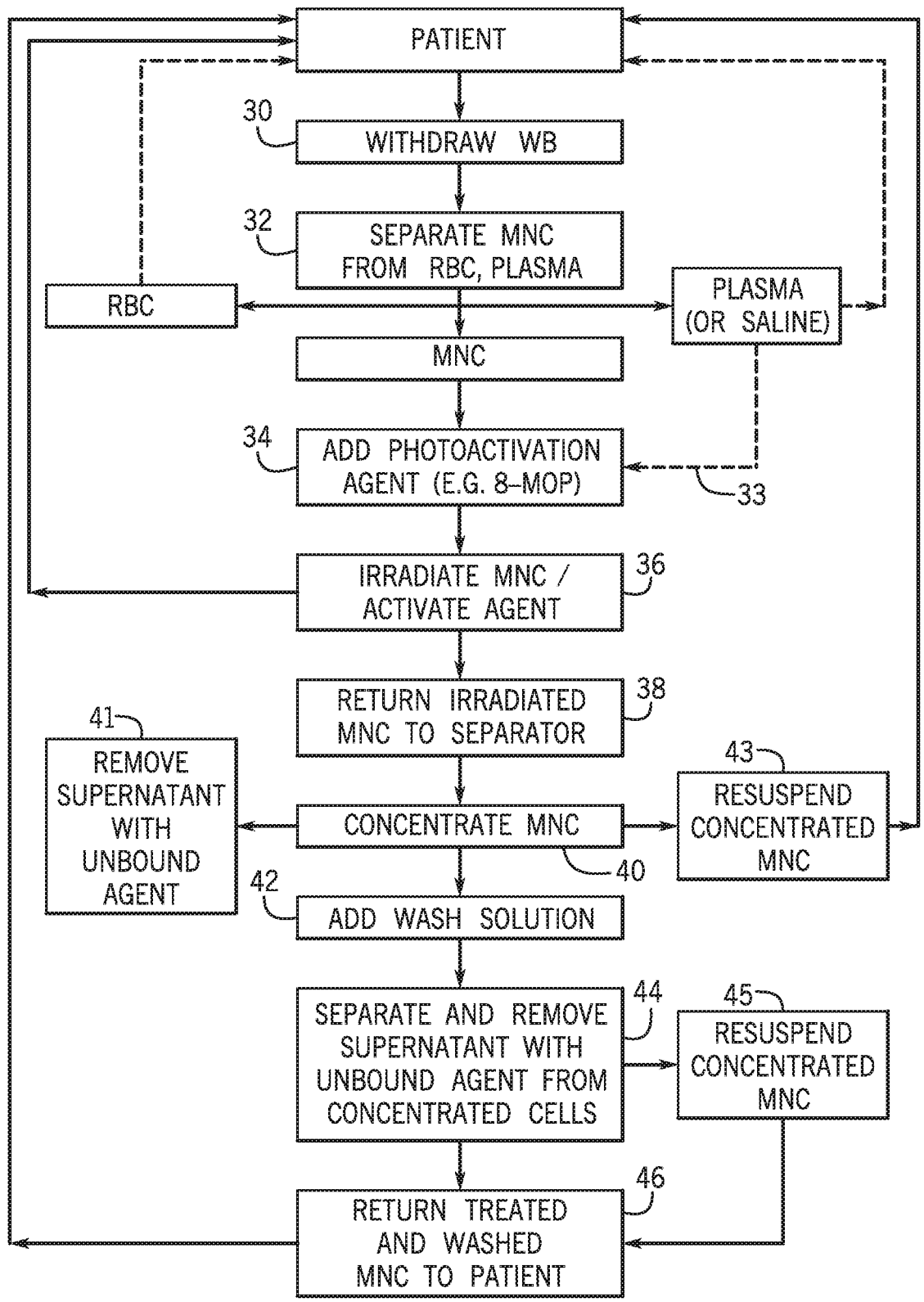
FIG. 5 is a flow chart setting forth a portion of the steps of the method of a photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the blood source. Whole blood may first be withdrawn from a blood source (step 30) through inlet needle 70 and introduced into the separation chamber 12 of container 14 of processing set 200, where the whole blood is subjected to, for example, a centrifugal field. The centrifugal field may separate the target cell population, i.e., mononuclear cells, from red blood cells, platelets and plasma (step 32). The components such as red blood cells and platelets may be returned to the blood source or may be diverted to a container (e.g., container 67) for further processing. Collection of the mononuclear cells may proceed in one or more cycles, with the number of processing cycles conducted in a given therapeutic procedure depending upon the total volume of MNCs to be collected. Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UV light device followed by subsequent reinfusion of the treated cells to a blood source. During such offline methods, when the cells are transferred from the apheresis device to the irradiation device (which device may be located in another room or laboratory), communication with the blood source is severed and the cells detached from the blood source.

Collected target cells may be concentrated, diluted, or otherwise processed in preparation for irradiation within collection/illumination container 68 (FIG. 4). For example, collected target cells may be diluted with plasma and/or saline, e.g., at step 33 of FIG. 5, to achieve a desired hematocrit. Collected target cells may also be combined with a suitable photoactivation agent, e.g., step 34 of FIG. 5, in preparation for irradiation.

Figure 6:
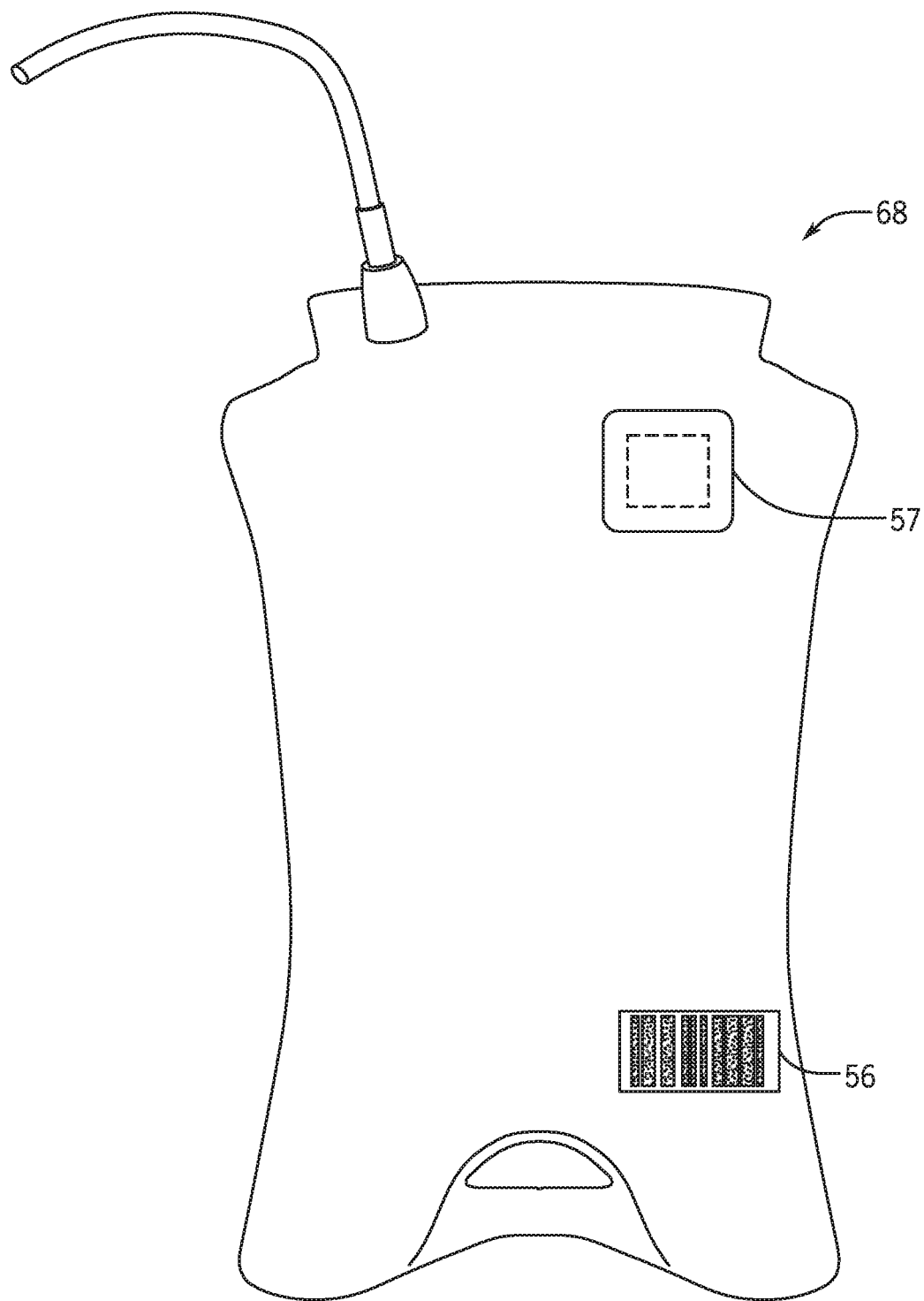
FIG. 6 shows an illumination container comprising features useful for labeling, tracking, and/or authenticating disposable components, according to an exemplary embodiment.

FIG. 6 shows an illumination container comprising features useful for labeling, tracking, and/or authenticating disposable components, according to an exemplary embodiment. In one embodiment, illumination container 68 that is part of disposable circuit 200 of FIG. 4 may comprise a tag 57 and/or a code 56 useful in preventing damage, alteration, falsification, and/or reuse of container 68 and/or any part of disposable circuit 200. Incorporating the tag 57 and/or code 56 onto container 68 may also prevent use of an otherwise legitimate disposable circuit intended for a different procedure performed by the system 5, separation component 10, and/or treatment component 20 (FIG. 1). For example, the system 5 may be programmed with a variety of other procedures, e.g., MNC collection (without photopheresis), platelet collection, offline photopheresis, etc., with each procedure having a corresponding and different disposable circuit. In an embodiment in which an authentication protocol is initiated for, e.g., an online photopheresis procedure, a user may be prevented from attempting to perform the online photopheresis procedure with a disposable circuit meant for, e.g., MNC collection, by scanning for the tag 57 and/or code 56 on container 68 to verify correctness of procedure and disposable circuit.

Tag 57 and/or code 56 may preferably maintain structural integrity during any storage period of container 68. The term "code" may be understood as an identification feature that provides relatively high labeling capacity or serialization. For example, a code may contain information decodable by a computer that may recognize a product and its details by cross-checking with established reference codes in a database or data repository. The term "tag" may be understood as an identification feature that provides limited labeling capacity and may be recognized by a computer but not decodable with information by the computer. For example, a tag may be used for simple authentication and/or tracking but may contain minimal information regarding details of the specific product.

In one embodiment, a compound with characteristic optical emission in response to specific irradiation may be used for the tag 57 and/or code 56 of container 68. A compound with characteristic optical emission may be described as a material that is reversibly or irreversibly transformed by light at certain excitation wavelengths to generate emission at a different wavelength or intensity than prior to transformation. Transformation may comprise isomerization, formation of color centers in crystalline salts, breaking or creation of covalent bonds (e.g., cross-linking in polymers), etc. For example, in an embodiment in which UV light is used to irradiate container 68 and its contents, a material that is transformed by UV light may be used. Examples of UV-sensitive materials resulting in generation of emission at a different wavelength or intensity than prior to transformation include photochromic ink, various coumarin derivatives, diarylethene derivatives incorporating trimethylsilyl (TMS) groups, ionic halide salts, lithium pentacosa-10,12-diynoic acid, and polyacetylene monomers.

Figure 7:
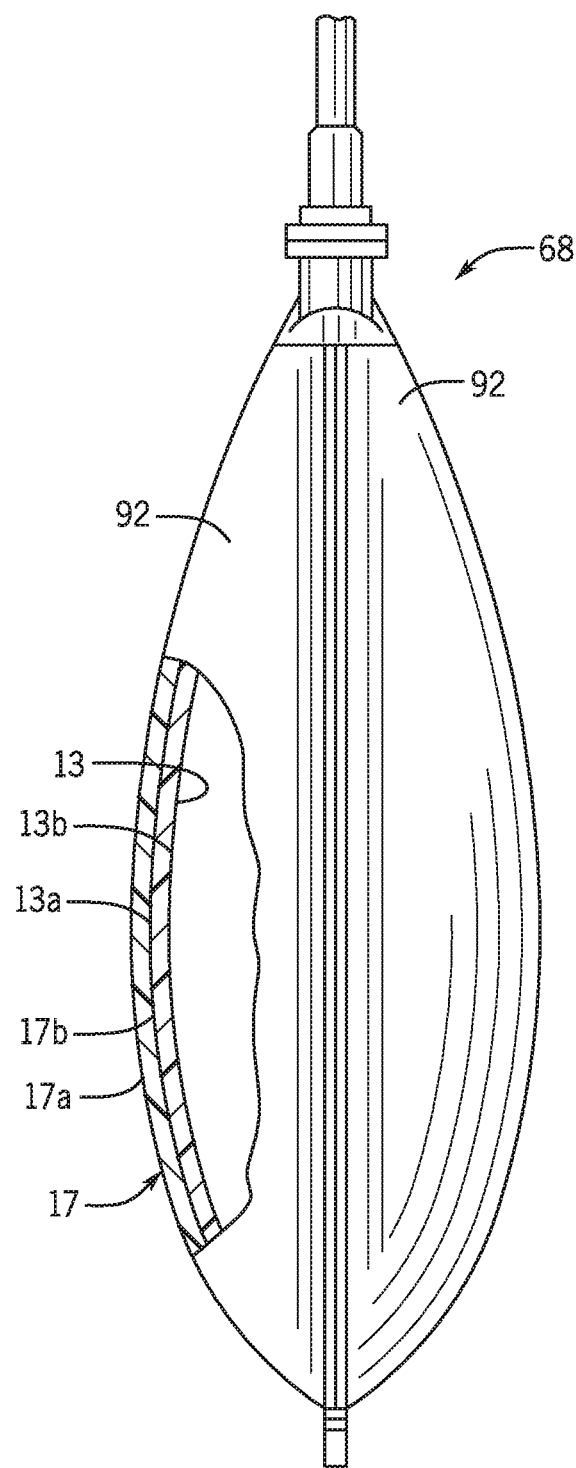
FIG. 7 shows a side view of the illumination container of FIG. 6, according to an exemplary embodiment.

A select molecule or combination of molecules with characteristic optical emission (hereinafter "photo-reactive entity") may be dissolved in a solvent or ink suitable for printing and/or coating on a medical device disposable component, such as container 68 (FIG. 4). In one embodiment a coating material such the Rad-Sure product available from International Specialty Products may be used. A design, code, or pattern ("identifiable feature") made visible or invisible by the photo-reactive entity may be sensed, recognized, and/or decoded before, during, and/or after irradiation. In an embodiment in which the disposable component to be tagged/coded is a fluid container such as the container 68 of FIG. 4, the substrate upon which the identifiable feature may be printed may be an inner or outer surface of the container 68. FIG. 7 shows a side view of container 68, according to an exemplary embodiment. In one embodiment, container 68 comprising container walls 92 may be made of a single layer of a polymer material, such as PVC or non-PVC polymer or polymer blend. In such a case, the identifiable feature may be printed or attached directly on the wall 92 of container 68. In another embodiment, container wall 92 may be made of a multiple sheet laminate wherein an inner layer 13 is made of one material and outer layer 17 is made of a different material. In such a case, the substrate upon which the identifiable feature may be printed may be separate from inner layer 13 and outer layer 17 and be placed between layers and form a part of the container wall 92. In another multi-layer embodiment, the identifiable feature may be printed on outer surface 17a of outer layer 17, inner surface 17b of outer layer 17, outer layer 13a of inner layer 13, and/or inner surface 13b of inner layer 13. The label may be affixed by the manufacturer at the time of kit build. In embodiments in which the identifiable feature is printed on outer surface 17a or wall 92 the identifiable feature may be made available on separate labels that may be affixed to the container 68 at time of use.

Figure 8A:
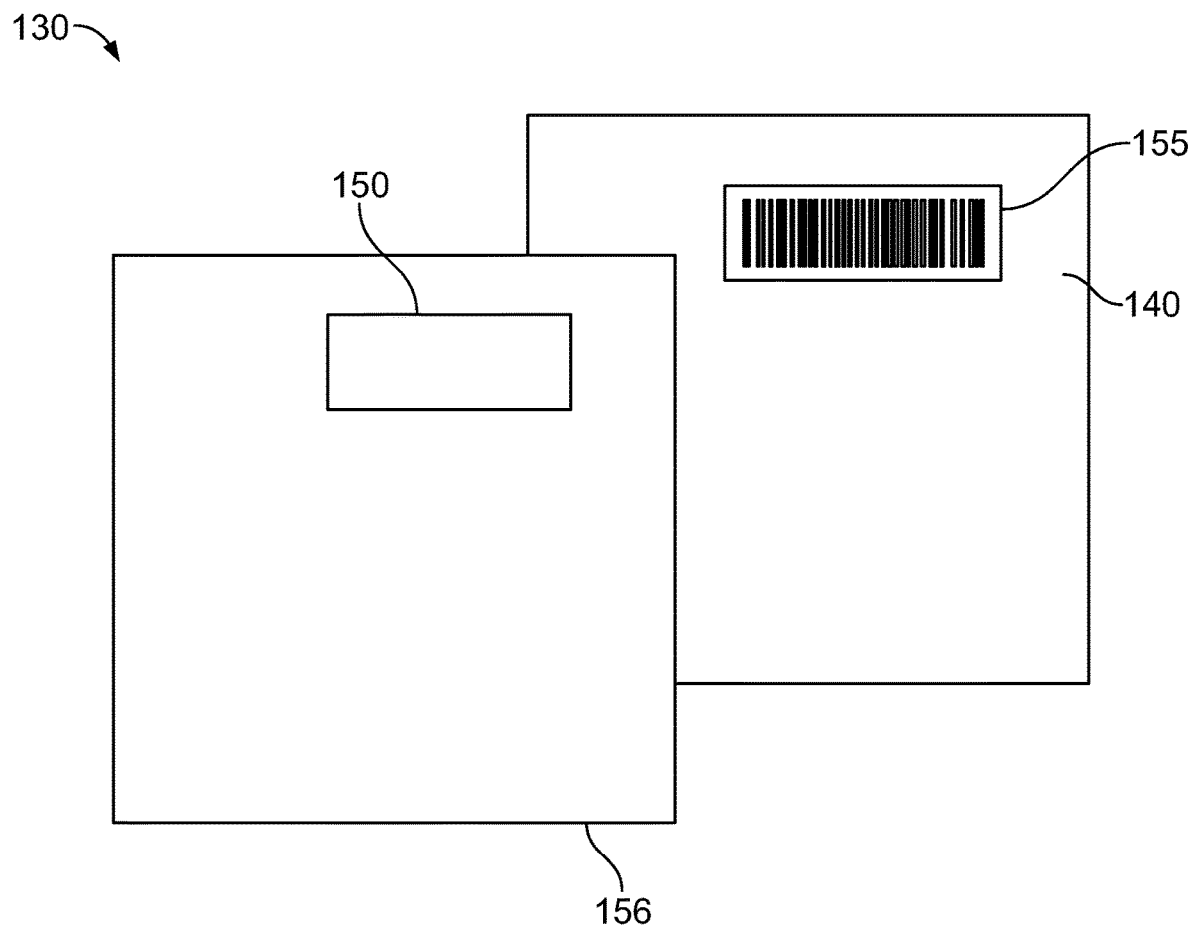
FIG. 8A is a diagrammatic illustration of one embodiment of a label comprising an identifiable feature, according to an exemplary embodiment.

FIG. 8A is a diagrammatic illustration of one embodiment of an identifiable feature. FIG. 8A shows a label 130 comprising a substrate 140 upon which an identifiable feature 155, e.g., bar code, tag, etc., may be printed. The identifiable feature 155 may be at a first state of visibility, e.g., visible to the naked eye, human- or machine-readable, prior to irradiation, and/or not comprise photo-reactive material. A photo-reactive entity 150 (e.g., UV-reactive) may be coated over the identifiable feature 155. The photo-reactive entity 150 may be coated directly over the identifiable feature 155 or may be overlaid via a transparent layer 156. In one embodiment, the photo-reactive entity 150 may comprise a polyacetylene monomer and/or lithium pentacosa-10,12-diynoic acid. In an embodiment in which lithium pentacosa-10,12-diynoic acid is used, the salt may be mixed with gelatin. The photo-reactive entity 150 may comprise different ratios of gelatin and salt as well as varying thickness of coating based on the desired sensitivity to different intensities of irradiation. In one embodiment, a 1:1 by weight mixture of gelatin and the lithium salt may be used. In one embodiment, the photo-reactive coating may comprise a thickness of about 20 microns. In one embodiment, prior to irradiation and/or at UV radiation levels less than about 1 $J/cm^2$, the photo-reactive entity 150 may be colorless or a light color, e.g., yellow. Between UV irradiation levels of about 1-10 $J/cm^2$, the photo-reactive entity 150 may develop some color but not be fully opaque. At UV levels above about 10 $J/cm^2$, the photo-reactive entity 150 may fully obscure the identifiable feature 155 from being readable by the naked eye or by a machine. When the identifiable feature 155 is not readable by the naked eye or machine, the identifiable feature 155 may be characterized as being in a second state of visibility different from the first state of visibility.

Figure 8B:
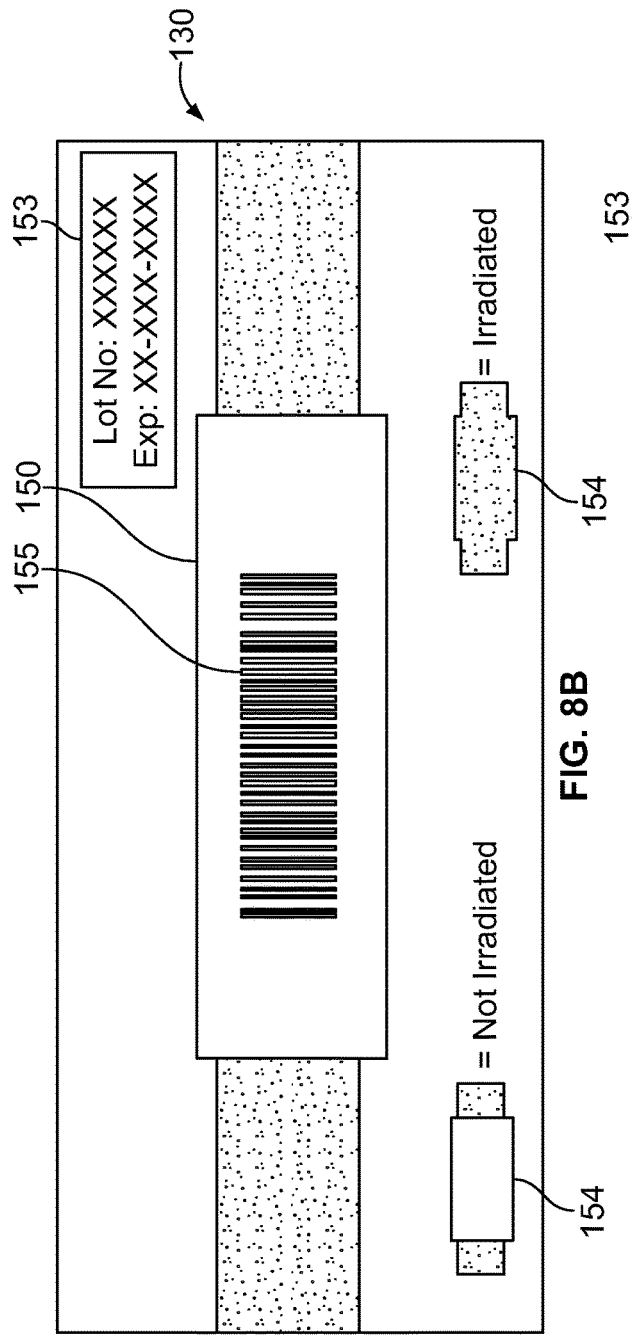
FIGS. 8B and 8C respectively illustrate the label of FIG. 8A before and after irradiation, according to an exemplary embodiment.
Figure 8C:
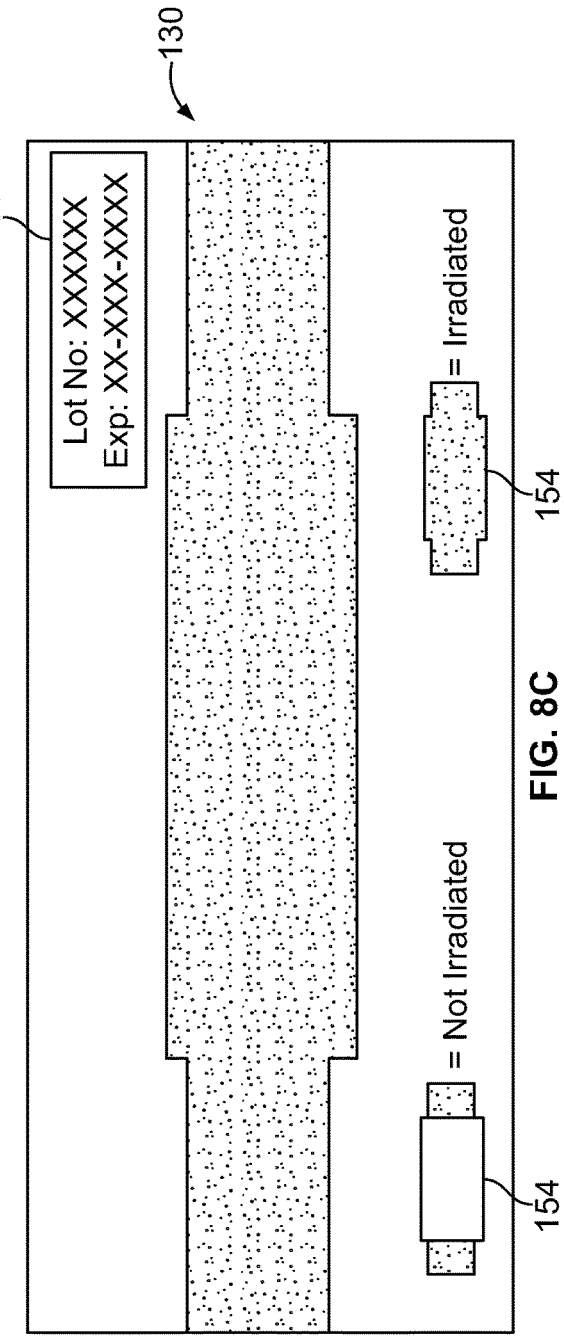

FIGS. 8B and 8C respectively illustrate labels prior to irradiation and subsequent to irradiation, according to an exemplary embodiment. FIG. 8B shows the label 130 of FIG. 8A prior to irradiation in which the identifiable feature 155, e.g., barcode, is visible and machine-readable because the photo-reactive entity 150 is yet colorless or light-colored in the absence of irradiation. Upon application of at least 10 $J/cm^2$ of UV, the photo-reactive entity 150 may turn fully opaque or dark-colored (FIG. 8C) to render the identifiable feature 155 not visible or machine-readable. The label 130 may contain other useful information 153, such as product manufacturer name, expiration date, lot number, product code, etc. The label 130 may also contain a legend 154 intended to provide indicia to a user whether irradiation has occurred at an appropriate step of the procedure and/or whether the correct dosage of irradiation has been applied.

Other embodiments may not incorporate a coating to obscure the identifiable feature, such as an embodiment in which the identifiable feature itself comprises photo-reactive material. For example, a bar code may be printed in the photo-reactive material and be invisible prior to irradiation and be visible during and after irradiation. In one embodiment, the identifiable feature may be unreadable at UV radiation levels less than about 1 $J/cm^2$ and fully readable at UV levels above about 10 $J/cm^2$.

Referring to FIG. 6, in one embodiment, both a tag 57 and a code 56 may be incorporated onto the container 68. In one embodiment, the tag 57 may comprise a RFID tag that uniquely pairs the container 68 with one irradiation procedure of the irradiation device 20 (FIG. 1). The unique identifier of the RFID tag may be received and read by the irradiation device 20 to check whether the container 68 is an authorized container prior to proceeding with irradiation. The RFID device may utilize electrically erasable programmable read-only memory (EEPROM) to store authentication data.

Figure 9:
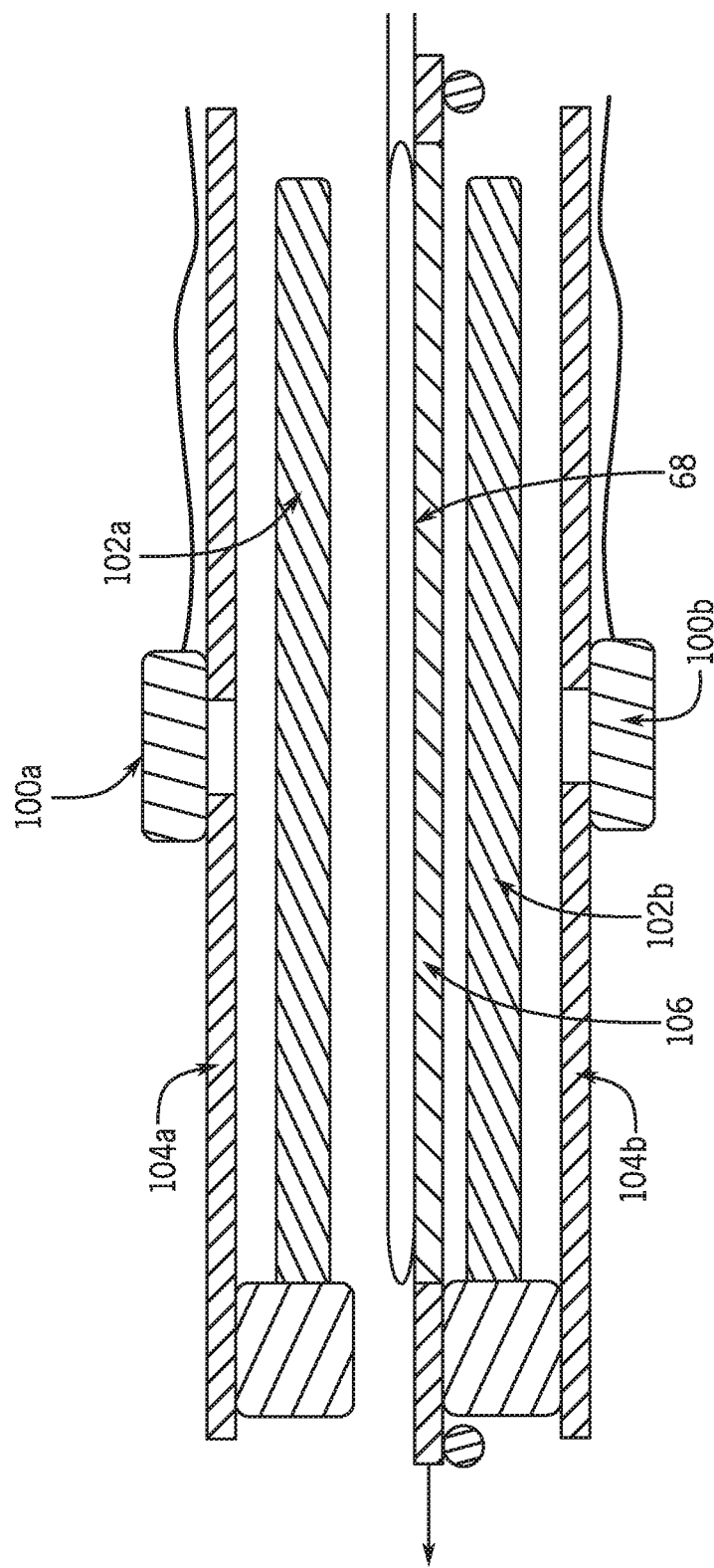
FIG. 9 is a cross-sectional view of the irradiation component of FIG. 1 holding an illumination container, according to an exemplary embodiment.

FIG. 9 shows a cross-sectional view of the irradiation component 20 of FIG. 1 holding container 68 having a RFID tag and a photo-identifiable code and containing a target cell product. A RFID reader 100a may be mounted above an upper bank 102a of a plurality of irradiation transmitters (e.g., UV light bulbs). The RFID reader 100a may be disposed at any location suitable for reading the RFID tag of container 68. A reflector plate 104a may be disposed above the upper bank 102a of light bulbs to reflect light emitted by the bulbs. An exposure plane 106 comprised of material transparent to the specific range of wavelengths emitted by the upper bank 102a (e.g., UV-transparent material) may be disposed below the upper bank 102a of light bulbs to support illumination container 68. A lower bank 102b of a plurality of irradiation transmitters, e.g., UV light bulbs, may be disposed below the exposure plane 106. A second reflector plate 104b may be disposed below the lower bank 102b of irradiation transmitters to reflect light emitted by the light bulbs. One or more barcode readers 100b may be mounted below the lower bank 102b of the light bulbs. The barcode reader 100b may be disposed at any location suitable for reading the barcode of container 68, including, e.g., above the upper bank 102a of UV bulbs. The irradiation device 20 may include any number of RFID readers 100a and barcode readers 100b, depending on the number of the tags and/or codes, and the readers 100a, 100b, may be disposed according to a predetermined layout of tags and/or codes on the container 68.

Figure 10A:
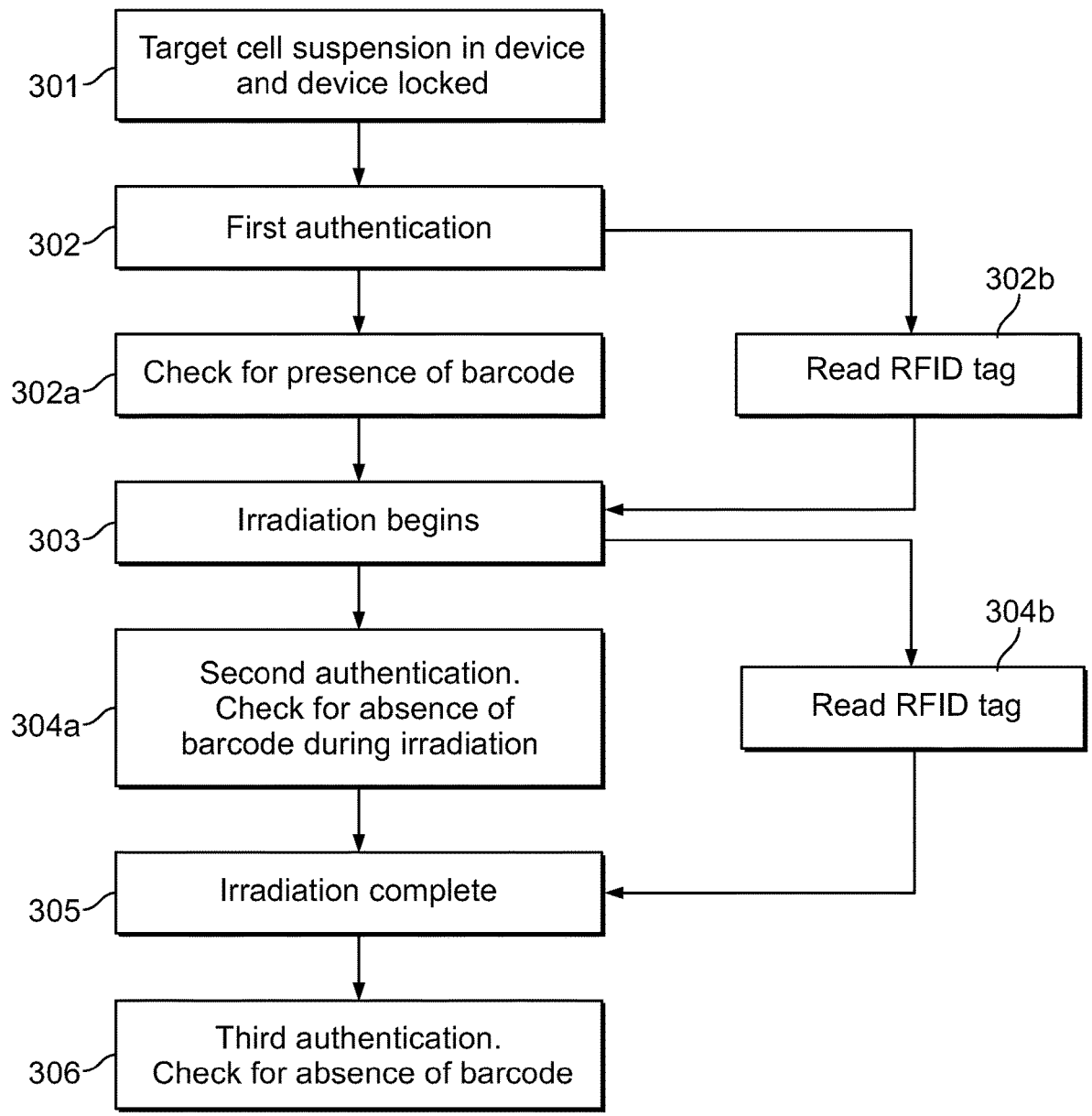
FIGS. 10A and 10B are flow charts each setting forth a method for authenticating a disposable component for photopheresis, according to an exemplary embodiment.

FIG. 10A depicts one embodiment of a method for authenticating a disposable component for photopheresis using the label depicted in FIGS. 8B and 8C. At step 301, container 68 (FIG. 4) containing target cells to be irradiated may be loaded into the irradiation device 20 (FIG. 1) and the door locked prior to beginning irradiation. The device 20 may be configured to lock out access to the container 68 throughout the authentication process. At step 302, the first authentication step may initiate, in which a barcode reader 100b checks at step 302a for the presence and authenticity of barcode 155 (FIG. 8B). The barcode 155 may be one of many serialized or unique barcodes that may be compared by the system against a remote data repository to ensure each disposable unit, e.g., container 68, is used only once. The first authentication step may also comprise the RFID reader 100a checking at step 302b for the RFID tag 57 (FIG. 6). Incorporating two separate authentications with RFID and the barcode may be useful for increasing the difficulty of counterfeiting and reuse of the container 68 and increasing the difficulty of bypassing the authentication mechanisms. The ECP system 5 may be configured to generate a response action if either step 302a or step 302b fails. The response action may comprise the processing circuit of the ECP system terminating the procedure, notifying an operator to load an authorized container, etc. At step 303 irradiation may begin. Once irradiation levels reach a threshold determined by the reactiveness of the photo-reactive entity 150 of label 130, the device 20 may perform a second authentication at step 304a in which the barcode reader 100b checks for the absence of the barcode 155, as depicted in FIG. 8C. The second authentication step may also comprise the RFID reader 100a checking at step 304b for the RFID tag 57. The system 5 may be configured to generate a response action if either step 304a or step 304b fails. If the second authentication step is successfully completed, the system may proceed to completion of the irradiation therapy at step 305. At step 306, the device 20 may perform a last authentication step in which the barcode reader 100b checks again for the absence of the barcode 155. A reappearance of the barcode 155 readable by the reader 100b may trigger a response action in which the remainder of the procedure is terminated or an alert is transmitted to an authorized user.

Figure 10B:
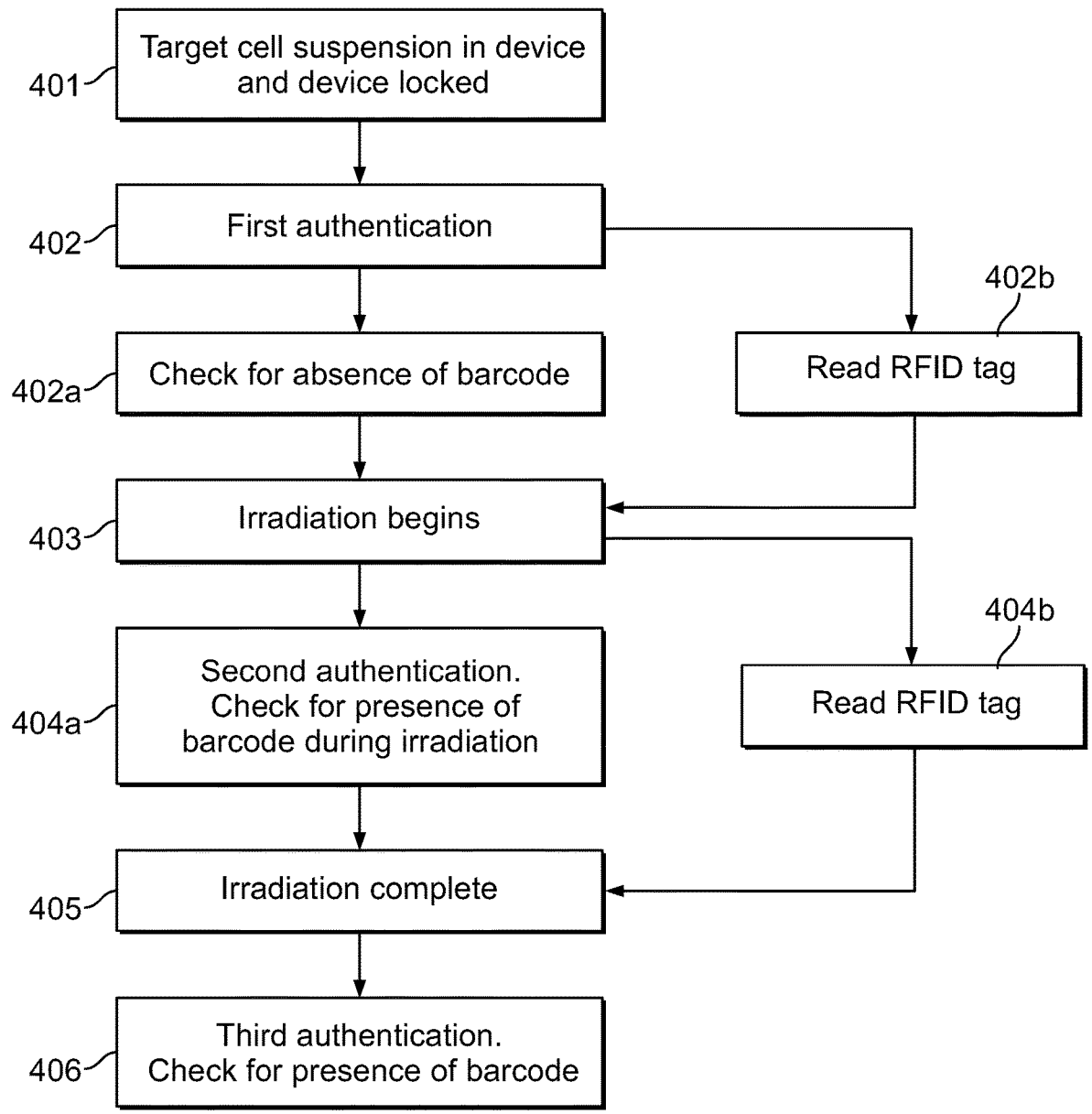

FIG. 10B depicts a method for authenticating a disposable component for photopheresis using a label comprising a bar code printed in photo-reactive material that is invisible prior to irradiation and visible during and after irradiation. At step 401, container 68 containing target cells to be irradiated may be loaded into the irradiation device 20 and the door locked prior to beginning irradiation. The device 20 may be configured to lock out access to the container 68 throughout the authentication process. At step 402, the first authentication step may initiate, in which a barcode reader 100b checks at step 402a for the absence of a barcode. The first authentication step may also comprise the RFID reader 100a checking at step 402b for a RFID tag. The ECP system 5 may be configured to generate a response action if either step 402a or step 402b fails. The response action may comprise the processing circuit of the ECP system terminating the procedure, notifying an operator to load an authentic container, etc. At step 403 irradiation may begin. Once irradiation levels reach a threshold determined by the reactiveness of the photo-reactive material of the barcode, the device 20 may perform a second authentication at step 404a in which the barcode reader 100b checks for the presence and authenticity of the barcode. The barcode may be one of many serialized or unique barcodes that may be compared by the system against a remote data repository to ensure each disposable unit, e.g., container 68, is used only once. The second authentication step may also comprise the RFID reader 100a checking at step 404b for the RFID tag. The system may be configured to generate a response action if either step 404a or step 404b fails. If the second authentication step is successfully completed, the system may proceed to completion of the irradiation therapy at step 405. At step 406, the device 20 may perform a last authentication step in which the barcode reader 100b checks again for the presence and authenticity of the barcode. A disappearance of the barcode readable by the reader 100b may trigger a response action in which the remainder of the procedure is terminated or an alert is transmitted to an authorized user.

Without limiting the foregoing description, in accordance with one aspect of the subject matter herein, there is provided a medical device verification system for an extracorporeal photopheresis procedure comprising a reusable irradiation device comprising a UV light source and a scanner. A fluid circuit is configured to cooperatively associate with the reusable irradiation device, the fluid circuit comprising a disposable cell suspension container having a photo-reactive label comprising an identifiable code. The identifiable code is unobscured to the scanner when the label in a first state and is obscured to the scanner when the label is in a second state. A programmable controller for the photopheresis procedure configured to receive a first input from the scanner prior to an irradiation step, the first input comprising identification of a state of the label. Based on receiving the first input from the scanner identifying the first state of the label, the irradiation step is performed by irradiating the disposable cell suspension container for a predetermined period of time at or above the threshold UV irradiation level. A second input is received from the scanner during the irradiation step, the second input comprising identification of a state of the label. Based on receiving the second input from the scanner identifying the second state of the label, the irradiation step is continued. A response action is provided if the first input comprises identification of the second state of the label and/or if the second input comprises identification of the first state of the label.

In accordance with a second aspect which may be used or combined with the immediately preceding aspect, the photo-reactive label comprises a photo-reactive material directly coated over the identifiable code or disposed atop a transparent layer overlaid over the identifiable code.

In accordance with a third aspect which may be used or combined with any of the preceding aspects, the photo-reactive label comprises a photo-reactive material comprising a polyacetylene monomer and/or lithium pentacosa-10, 12-diynoic acid.

In accordance with a fourth aspect which may be used or combined with any of the preceding aspects, the threshold UV irradiation level is 10 J/cm$^2$.

In accordance with a fifth aspect which may be used or combined with any of the preceding aspects, the reusable irradiation device further comprises a RFID reader. The disposable cell suspension container further comprises a RFID tag that uniquely pairs the disposable cell suspension container with one irradiation procedure of the reusable irradiation device. The programmable controller is further configured to receive a third input from the RFID reader indicating recognition of the RFID tag as an authorized RFID tag and proceed with the extracorporeal photopheresis procedure only if the third input is received. A response action is provided if the third input is not received.

In accordance with a sixth aspect which may be used or combined with any of the preceding aspects, the response action comprises at least one of terminating the extracorporeal photopheresis procedure, terminating irradiation, notifying an operator to load an authorized container, and transmitting an alert to an authorized user.

In accordance with a seventh aspect which may be used or combined with any of the preceding aspects, the programmable controller for the photopheresis procedure is further configured to receive a third input from the scanner after the irradiation step, the third input comprising identification of a state of the label. The response action is provided if the third input comprises identification of the first state of the label.

In accordance with an eighth aspect, there is provided a medical device verification system for an extracorporeal photopheresis procedure. A reusable irradiation device comprises a UV light source and a scanner. A fluid circuit is configured to cooperatively associate with the reusable irradiation device, the fluid circuit comprising a disposable cell suspension container having a photo-reactive label comprising an identifiable code. The identifiable code is obscured to the scanner when the label is in a first state and unobscured to the scanner when the label is in a second state. A programmable controller for the photopheresis procedure is configured to receive a first input from the scanner prior to an irradiation step, the first input comprising identification of a state of the label. Based on receiving the first input from the scanner identifying the first state of the label, the irradiation step is performed by irradiating the disposable cell suspension container for a predetermined period of time at or above the threshold UV irradiation level. A second input from the scanner is received during the irradiation step, the second input comprising identification of a state of the label. Based on receiving the second input from the scanner identifying the second state of the label, the irradiation step is continued. A response action is provided if the first input comprises identification of the second state of the label and/or if the second input comprises identification of the first state of the label.

In accordance with a ninth aspect which may be used or combined with the eighth aspect, the identifiable code is printed with a photo-reactive material.

In accordance with a tenth aspect which may be used or combined with any of the eighth and ninth aspects, the photo-reactive label comprises a photo-reactive material comprising a polyacetylene monomer and/or lithium pentacosa-10,12-diynoic acid.

In accordance with an eleventh aspect which may be used or combined with any of the eighth through tenth aspects, the threshold UV irradiation level is 10 J/cm$^2$.

In accordance with a twelfth aspect which may be used or combined with any of the eighth through eleventh aspects, the reusable irradiation device further comprises a RFID reader, wherein the disposable cell suspension container further comprises a RFID tag that uniquely pairs the disposable cell suspension container with one irradiation procedure of the reusable irradiation device. The programmable controller is further configured to receive a third input from the RFID reader indicating recognition of the RFID tag as an authorized RFID tag and proceed with the extracorporeal photopheresis procedure only if the third input is received. A response action is provided if the third input is not received.

In accordance with a thirteenth aspect which may be used or combined with any of the eighth through twelfth aspects, the response action comprises at least one of terminating the extracorporeal photopheresis procedure, terminating irradiation, notifying an operator to load an authorized container, and transmitting an alert to an authorized user.

In accordance with a fourteenth aspect which may be used or combined with any of the eighth through thirteenth aspects, the programmable controller for the photopheresis procedure is further configured to receive a third input from the scanner after the irradiation step, the third input comprising identification of a state of the label. The response action is provided if the third input comprises identification of the first state of the label.

In accordance with a fifteenth aspect, there is provided a computer-implemented method for approving a medical device disposable component used in an extracorporeal photopheresis procedure. A reusable irradiation device comprising a UV light source and a scanner is provided. The reusable irradiation device is configured to irradiate a target cell suspension in an irradiation step. A photo-reactive label is provided comprising an identifiable code on a disposable component configured for irradiation within the reusable irradiation device and UV light source. The identifiable code is at a first state of visibility to the scanner when not having been exposed to a threshold UV irradiation level and a second state of visibility to the scanner after being exposed to the threshold UV irradiation level. A programmable controller is provided configured to receive a first input from the scanner prior to the irradiation step, the first input comprising identification of a state of visibility of the label, and configured to receive a second input from the scanner during the irradiation step, the second input comprising identification of a state of visibility of the label. Based on receiving the first input from the scanner identifying the first state of visibility of the label, the irradiation step is performed by irradiating the disposable cell suspension container for a predetermined period of time at or above the threshold UV irradiation level. Based on receiving the second input from the scanner identifying the second state of visibility of the label, the irradiation step is continued. A response action is provided if the first input comprises identification of the second state of visibility of the label and/or if the second input comprises identification of the first state of visibility of the label.

In accordance with a sixteenth aspect which may be used or combined with the fifteenth aspect, the photo-reactive label comprises a photo-reactive material comprising a polyacetylene monomer and/or lithium pentacosa-10,12-diynoic acid.

In accordance with a seventeenth aspect which may be used or combined with any of the fifteenth and sixteenth aspects, the threshold UV irradiation level is 10 J/cm$^2$.

In accordance with an eighteenth aspect which may be used or combined with any of the fifteenth through seventeenth aspects, the reusable irradiation device further comprises a RFID reader. The disposable component further comprises a RFID tag that uniquely pairs the disposable component with one irradiation procedure of the reusable irradiation device. A third input is received via the programmable controller from the RFID reader indicating recognition of the RFID tag as an authorized RFID tag. The extracorporeal photopheresis procedure proceeds only if the third input is received. The response action is provided if the third input is not received.

In accordance with a nineteenth aspect which may be used or combined with any of the fifteenth through eighteenth aspects, the response action comprises at least one of terminating the extracorporeal photopheresis procedure, terminating irradiation, notifying an operator to load an authorized container, and transmitting an alert to an authorized user.

In accordance with a twentieth aspect which may be used or combined with any of the fifteenth through nineteenth aspects, a third input is received via the programmable controller from the scanner after the irradiation step, the third input comprising identification of a state of visibility of the label. The response action is provided if the third input comprises identification of the first state of visibility of the label.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A medical device verification system for an extracorporeal photopheresis procedure comprising:
   a reusable irradiation device comprising a UV light source and a scanner;
   a fluid circuit configured to cooperatively associate with the reusable irradiation device, the fluid circuit comprising a disposable cell suspension container having a photo-reactive label comprising an identifiable code, wherein the identifiable code is at a first state of visibility to the scanner when not having been exposed to a threshold UV irradiation level and a second state of visibility to the scanner after being exposed to the threshold UV irradiation level; and
   a programmable controller for the photopheresis procedure configured to:
      receive a first input from the scanner prior to an irradiation step of the photopheresis procedure, the first input comprising identification of a state of visibility of the label;
      based on receiving the first input from the scanner identifying the first state of visibility of the label, perform the irradiation step by irradiating the disposable cell suspension container for a predetermined period of time at or above the threshold UV irradiation level;
      receive a second input from the scanner during the irradiation step, the second input comprising identification of a state of visibility of the label;
      based on receiving the second input from the scanner identifying the second state of visibility of the label, continue the irradiation step; and
      provide a response action if the first input comprises identification of the second state of visibility of the label and/or if the second input comprises identification of the first state of visibility of the label,
      wherein the response action comprises at least one of terminating the extracorporeal photopheresis procedure, terminating irradiation, notifying an operator to load an authorized container, and transmitting an alert to an authorized user.

2. The system of claim 1, wherein the photo-reactive label comprises a photo-reactive material directly coated over the identifiable code or disposed atop a transparent layer overlaid over the identifiable code.

3. The system of claim 1, wherein the photo-reactive label comprises a photo-reactive material comprising a polyacetylene monomer and/or lithium pentacosa-10,12-diynoic acid.

4. The system of claim 1, wherein the threshold UV irradiation level is 10 J/cm$^2$.

5. The system of claim 1, wherein the reusable irradiation device further comprises a RFID reader, wherein the disposable cell suspension container further comprises a RFID tag that uniquely pairs the disposable cell suspension container with one irradiation procedure of the reusable irradiation device, and wherein the programmable controller is further configured to:
   receive a third input from the RFID reader indicating recognition of the RFID tag as an authorized RFID tag and proceed with the extracorporeal photopheresis procedure only if the third input is received; and
   provide a response action if the third input is not received.

6. The system of claim 1, wherein the programmable controller for the photopheresis procedure is further configured to:
   receive a third input from the scanner after the irradiation step, the third input comprising identification of a state of the label; and
   provide the response action if the third input comprises identification of the first state of visibility of the label.

7. A medical device verification system for an extracorporeal photopheresis procedure comprising:
   a reusable irradiation device comprising a UV light source and a scanner;
   a fluid circuit configured to cooperatively associate with the reusable irradiation device, the fluid circuit comprising a disposable cell suspension container having a photo-reactive label comprising an identifiable code, wherein the identifiable code is obscured to the scanner when the label is in a first state and unobscured to the scanner when the label is in a second state; and a programmable controller for the photopheresis procedure configured to:
> receive a first input from the scanner prior to an irradiation step of the photopheresis procedure, the first input comprising identification of a state of the label;
> based on receiving the first input from the scanner identifying the first state of the label, perform the irradiation step by irradiating the disposable cell suspension container for a predetermined period of time at or above the threshold UV irradiation level;
> receive a second input from the scanner during the irradiation step, the second input comprising identification of a state of the label;
> based on receiving the second input from the scanner identifying the second state of the label, continue the irradiation step; and
> provide a response action if the first input comprises identification of the second state of the label and/or if the second input comprises identification of the first state of the label,
> wherein the response action comprises at least one of terminating the extracorporeal photopheresis procedure, terminating irradiation, notifying an operator to load an authorized container, and transmitting an alert to an authorized user.

8. The system of claim 7, wherein the identifiable code is printed with a photo-reactive material.

9. The system of claim 7, wherein the photo-reactive label comprises a photo-reactive material comprising a polyacetylene monomer and/or lithium pentacosa-10,12-diynoic acid.

10. The system of claim 7, wherein the threshold UV irradiation level is 10 J/cm$^2$.

11. The system of claim 7, wherein the reusable irradiation device further comprises a RFID reader, wherein the disposable cell suspension container further comprises a RFID tag that uniquely pairs the disposable cell suspension container with one irradiation procedure of the reusable irradiation device, and wherein the programmable controller is further configured to:
> receive a third input from the RFID reader indicating recognition of the RFID tag as an authorized RFID tag and proceed with the extracorporeal photopheresis procedure only if the third input is received; and
> provide a response action if the third input is not received.

12. The system of claim 7, wherein the programmable controller for the photopheresis procedure is further configured to:
> receive a third input from the scanner after the irradiation step, the third input comprising identification of a state of the label; and
> provide the response action if the third input comprises identification of the first state of the label.

13. A computer-implemented method for approving a medical device disposable component used in an extracorporeal photopheresis procedure comprising:
> providing a reusable irradiation device comprising a UV light source and a scanner, wherein the reusable irradiation device is configured to irradiate a target cell suspension in an irradiation step of the photopheresis procedure;
> providing a photo-reactive label comprising an identifiable code on a disposable cell suspension container configured for irradiation within the reusable irradiation device and UV light source, wherein the identifiable code is at a first state of visibility to the scanner when not having been exposed to a threshold UV irradiation level and a second state of visibility to the scanner after being exposed to the threshold UV irradiation level;
> providing a programmable controller configured to receive a first input from the scanner prior to the irradiation step, the first input comprising identification of a state of visibility of the label, and configured to receive a second input from the scanner during the irradiation step, the second input comprising identification of a state of visibility of the label;
> based on receiving the first input from the scanner identifying the first state of visibility of the label, performing the irradiation step by irradiating the disposable cell suspension container for a predetermined period of time at or above the threshold UV irradiation level;
> based on receiving the second input from the scanner identifying the second state of visibility of the label, continuing the irradiation step; and
> providing a response action if the first input comprises identification of the second state of visibility of the label and/or if the second input comprises identification of the first state of visibility of the label,
> wherein the response action comprises at least one of terminating the extracorporeal photopheresis procedure, terminating irradiation, notifying an operator to load an authorized container, and transmitting an alert to an authorized user.

14. The method of claim 13, wherein the photo-reactive label comprises a photo-reactive material comprising a polyacetylene monomer and/or lithium pentacosa-10,12-diynoic acid.

15. The method of claim 13, wherein the threshold UV irradiation level is 10 J/cm$^2$.

16. The method of claim 13, wherein the reusable irradiation device further comprises a RFID reader, wherein the disposable component further comprises a RFID tag that uniquely pairs the disposable component with one irradiation procedure of the reusable irradiation device, and comprising:
> receiving via the programmable controller a third input from the RFID reader indicating recognition of the RFID tag as an authorized RFID tag;
> proceeding with the extracorporeal photopheresis procedure only if the third input is received; and
> providing the response action if the third input is not received.

17. The method of claim 13, further comprising:
> receiving via the programmable controller after the irradiation step a third input from the scanner, the third input comprising identification of a state of visibility of the label; and
> providing the response action if the third input comprises identification of the first state of visibility of the label.

* * * * *